United States Patent
Kam et al.

(10) Patent No.: US 12,350,380 B1
(45) Date of Patent: Jul. 8, 2025

(54) ENTERIC COATING FOR TARGETING THE DUODENUM

(71) Applicant: Verily Life Sciences LLC, South San Francisco, CA (US)

(72) Inventors: Kimberly Kam, Orinda, CA (US); Martin Sheridan, Redwood City, CA (US); Angela DiCiccio, San Francisco, CA (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

(21) Appl. No.: 17/388,944

(22) Filed: Jul. 29, 2021

Related U.S. Application Data (60) Provisional application No. 63/058,750, filed on Jul. 30, 2020.

(51) Int. Cl.
*A61K 9/48* (2006.01)
*A61K 9/00* (2006.01)
*A61K 45/06* (2006.01)

(52) U.S. Cl.
CPC ............ *A61K 9/4891* (2013.01); *A61K 9/006* (2013.01); *A61K 9/0097* (2013.01); *A61K 45/06* (2013.01)

(58) Field of Classification Search
CPC .... A61K 9/4891; A61K 9/006; A61K 9/0097; A61K 45/06
See application file for complete search history.

(56) References Cited

U.S. PATENT DOCUMENTS

2021/0361919 A1 * 11/2021 Langer ................. A61B 5/6861
2022/0257855 A1 * 8/2022 Traverso ............. A61M 5/2033

FOREIGN PATENT DOCUMENTS

WO     WO-2017004000 A1 * 1/2017 ........... A61K 9/0004

\* cited by examiner

*Primary Examiner* — Robert A Wax
*Assistant Examiner* — Olga V. Tcherkasskaya
(74) *Attorney, Agent, or Firm* — Kilpatrick Townsend & Stockton LLP (57) ABSTRACT

A system for targeted delivery of a medicament to the gastrointestinal tract (e.g., selectively to the duodenum) of a subject. The system includes a medicament, a mucoadhesive layer at least partially surrounding the medicament, and an enteric coating encasing the medicament and mucoadhesive layer. The enteric coating comprises a material degradable by a pH of the GI tract and a material digestible by a lipase. Also provided are method of making and using the system for targeted delivery of a medicament to the gastrointestinal tract. Also provided are a system for deploying a medicament-containing needle system using an expanding element. The system includes a medicament-containing needle system and an expanding element within a capsule. The capsule is initially coated with an enteric coating. As the enteric coating degrades the expanding element absorbs fluid that enters the capsule and expands to deploy the medicament-containing needle system from the capsule.

17 Claims, 3 Drawing Sheets

ENTERIC COATING FOR TARGETING THE DUODENUM

CROSS-REFERENCE TO RELATED APPLICATIONS

This application claims benefit and priority to U.S. Provisional Patent Application No. 63/058,750, filed on Jul. 30, 2020, the disclosure of which is herein incorporated by reference in its entirety for all purposes.

TECHNICAL FIELD

The present disclosure generally relates to systems for delivering medicaments or other payloads inside a body, and more specifically, but not necessarily limited to, ingestible systems for delivery of a payload to some portion of a lining of a gastrointestinal tract.

BACKGROUND

A number of scientific methods have been developed in the medical field to attempt medicament deliver specifically to the human gastrointestinal (GI) tract. When coatings are used to target a portion of the GI tract, however, dissolution occurs in a gradient process before the targeted region is reached. In some cases a gradient dissolution process may be suitable for delivery of small molecule medicaments that may be absorbed at any point in the GI tract. However, in other cases, rapid dissolution (e.g., as a binary response) at the targeted point in the GI tract is desired to achieve the desired therapeutic effect or to avoid negative side effects required by high doses of the medicament. It is therefore desirable to provide a medicament delivery device capable of accurately and precisely targeting a particular part of the GI tract, the duodenum.

SUMMARY

Various examples of the present disclosure are directed to systems for targeted delivery to the duodenum of a subject.

In one aspect of the present disclosure, a system for targeted delivery to a duodenum is provided. In certain embodiments, the system for targeted delivery to a duodenum, comprises a medicament, a mucoadhesive layer; and an enteric coating encasing the medicament, wherein the enteric coating comprises at least a material degradable by a pH of the duodenum, and at least a material digestible by a lipase. In certain aspects, the system for targeted delivery of a medicament further comprises a rigid material layer. In some cases, the material digestible by a lipase comprises a wax material, and the material degradable by a pH of the duodenum comprises a polymer (e.g., a polymer comprising a gelatin paper or sheets, rice paper or sheets, polylactic acid, nylon, polyester, PVA (polyvinyl alcohol), polymethacrylates, shellac, hydroxypropylmethylcellulose acetate succinate (HPMCAS), or other corn-based polymers). In certain aspects, the enteric coating encasing the medicament does not degrade in a human stomach. Optionally, the enteric coating encasing the medicament degrades in less than one minute when the medicament arrives at the duodenum. In some examples, the enteric coating encasing the medicament degrades at a rate of from 5 milligrams per cubic centimeter per minute ((mg/cm$^3$)/min) to 26 (mg/cm$^3$)/min. In certain embodiments, the enteric coating encasing the medicament degrades to expose the mucoadhesive layer and the mucoadhesive layer attaches the system for targeted delivery to a wall of the GI system (e.g., to a wall of the duodenum). In certain aspects, the enteric coating encasing the medicament degrades to expose the medicament, and the medicament is actively administered into or passively absorbed by the wall of the duodenum. Active administration optionally comprises a needle delivery system that, upon release, drives needles into engagement with a wall of the GI tract so as to facilitate delivery of the medicament contained therein.

Also described herein is a method of making the system for targeted delivery, including providing an enteric coating to a medicament or a medicament-containing needle delivery system, comprising providing the medicament or medicament-containing needle delivery system, coating the medicament or medicament-containing needle delivery system with a mucoadhesive layer to provide a mucoadhesive-coated medicament or medicament-containing needle delivery system, at least partially coating the mucoadhesive-coated medicament or medicament-containing needle delivery system with at least a material degradable by a pH of the duodenum; and, at least partially coating the mucoadhesive-coated medicament or medicament-containing needle delivery system with at least a material digestible by a lipase. In some embodiments, at least partially coating the mucoadhesive-coated medicament or medicament-containing needle delivery system with at least a material degradable by a pH of the duodenum comprises at least partially coating the mucoadhesive-coated medicament or medicament-containing needle delivery system with a polymer. In certain embodiments, at least partially coating the mucoadhesive-coated medicament or medicament-containing needle delivery system with at least a material digestible by a lipase comprises at least partially coating the mucoadhesive-coated medicament or medicament-containing needle delivery system with a wax material. In some cases, at least partially coating the mucoadhesive-coated medicament or medicament-containing needle delivery system with at least a material degradable by a pH of the duodenum and at least partially coating the mucoadhesive-coated medicament or medicament-containing needle delivery system with at least a material digestible by a lipase comprises coating the mucoadhesive-coated medicament or medicament-containing needle delivery system with the material degradable by a pH of the duodenum and with the material digestible by a lipase in a 1 to 1 ratio (e.g., a 0.6 to 0.4 ratio, a 0.4 to 0.6 ratio, a 0.7 to 0.3 ratio, or a 0.3 to 0.7 ratio). In certain embodiments, at least partially coating the mucoadhesive-coated medicament or medicament-containing needle delivery system with at least a material degradable by a pH of the duodenum and at least partially coating the mucoadhesive-coated medicament or medicament-containing needle delivery system with at least a material digestible by a lipase comprises a duodenum-targeted medicament delivery device.

Also described herein is a method of targeting delivery to a duodenum, comprising providing a medicament or medicament-containing needle delivery system, coating the medicament or medicament-containing needle delivery system with a mucoadhesive layer, coating the medicament or medicament-containing needle delivery system coated with the mucoadhesive layer with an enteric coating to provide a duodenum targeting medicament; and, administering the duodenum targeting medicament to a subject. In certain embodiments, administering the duodenum targeting medicament to a subject comprises the subject swallowing the duodenum targeting medicament, passing the duodenum targeting medicament through an esophagus of the subject, and passing the duodenum targeting medicament through a stomach of the subject into the duodenum of the subject.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples of systems for targeted delivery to a duodenum of a subject are provided. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, a subject may wish to take a dose of a medicament (e.g., biotherapeutic or other compound) without resorting to a syringe injection in the arm and potential accompanying discomfort or other concerns. To this end, the person may use a system according to this disclosure to provide the dosage. In this example, the system may be provided in pill or capsule form that the subject can swallow. Inside the pill or capsule are components capable of deploying within the body to effectively provide an internal administration of a payload. As the pill or capsule reaches a target portion of the gastrointestinal tract (such as the duodenum), a specialized coating of the pill or capsule dissolves or degrades sufficiently to break apart and allow release of a medicament or a medicament-containing needle delivery system.

Figure 1:
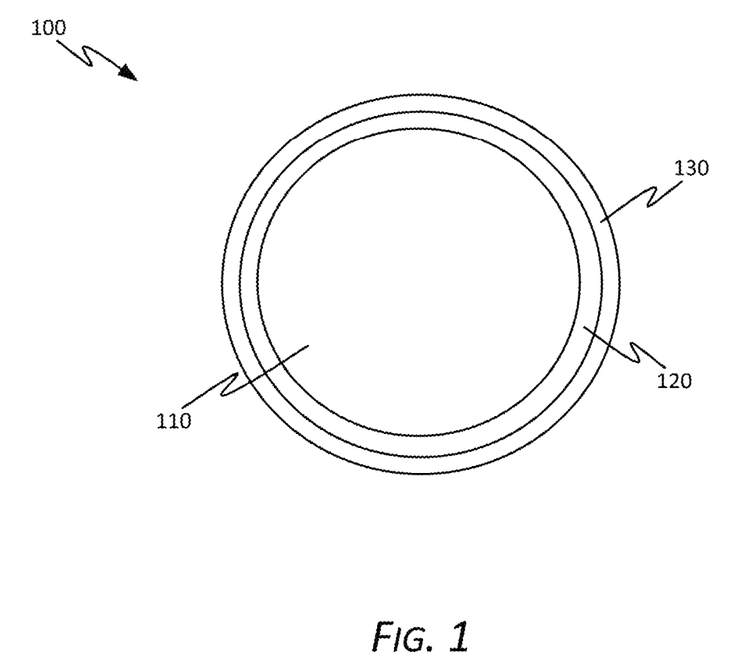
FIG. 1 shows a cross-sectional view of a system for targeted delivery comprising a medicament, a mucoadhesive layer, and an enteric coating.

Turning now to the drawings (which are rendered for purposes of illustrating principles and thus may not necessarily be to scale), FIG. 1 shows an embodiment of a system for targeted delivery to a duodenum 100. The medicament 110 is encased by a mucoadhesive layer 120 and an enteric coating 130 in the depicted arrangement, although in some instances, the mucoadhesive layer 120 is omitted. In certain aspects, the mucoadhesive layer 120 can be pectin, sodium carboxymethyl cellulose (Na-CMC), and/or carbopol. The mucoadhesive layer 120 can be used to attach the medicament 110 to the wall of the duodenum to provide a duodenum targeting medicament. In other aspects, an aspect ratio of the system for targeted delivery to a duodenum 100 can be used to orient and align the medicament 110 within the duodenum. For example, the system for targeted delivery to a duodenum 100 can have a length that is greater than a diameter of the duodenum and a cross-sectional diameter that is less than or equal to the diameter of the duodenum such that the medicament 110 self-aligns into the duodenum.

As described herein, the enteric coating 130 can be a composition comprised of a combination of materials, including at least a material degradable by a pH of the duodenum, and at least a material digestible by a lipase. As described herein, the system for targeted delivery to the duodenum 100 allows the medicament 110 to pass through a subject's mouth, esophagus, and stomach without degrading or prematurely releasing its payload. When the system for targeted delivery to the duodenum 100 reaches the duodenum, the enteric coating 130 comprising a combination of the material degradable by the pH of the duodenum and the material digestible by a lipase can dissolve rapidly such that the medicament 110 is released in the duodenum.

Figure 2:
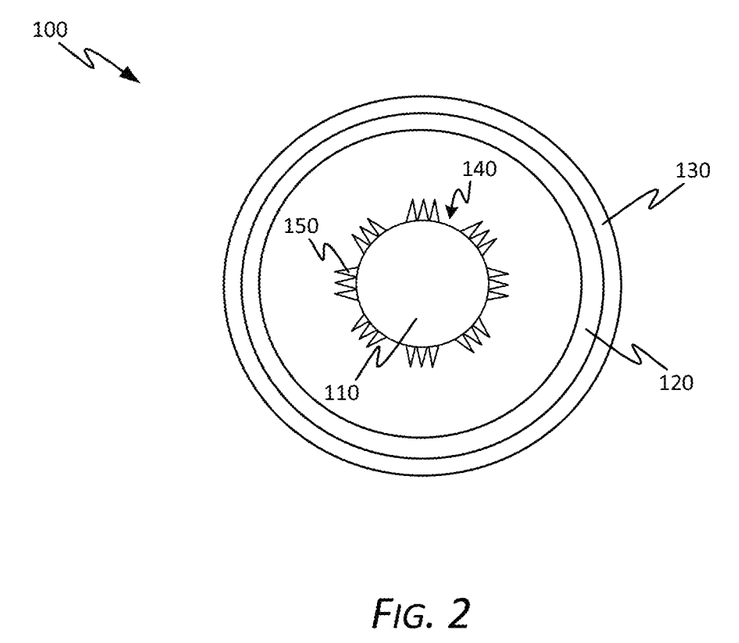
FIG. 2 shows a cross-sectional view of a system for targeted delivery comprising a medicament-containing needle delivery system, a mucoadhesive layer, and an enteric coating encasing the medicament-containing needle delivery system.

FIG. 2 shows an embodiment in which the medicament 110 is present in or with a needle delivery system 140. In this embodiment, the needle delivery system 140 is deployed or released so as to inject the medicament into the wall of the duodenum. The needle delivery system 140, along with the medicament 110, is encased by a mucoadhesive layer 120 and an enteric coating 130 in the depicted arrangement, although in some instances, the mucoadhesive layer 120 is omitted. In certain examples, the medicament is encased in a digestible waxy material 210 as shown in FIG. 2. The digestible waxy material 210 can be used to maintain an expanding element in a compressed position until the digestible waxy material is digested in the duodenum. As described herein, the enteric coating 130 can be comprised of a combination of materials, including at least a material degradable by a pH of the duodenum, and at least a material digestible by a lipase. The system for targeted delivery to the duodenum 100 allows the needle delivery system 140 associated with the medicament 110 to pass through a subject's mouth, esophagus, and stomach without degrading or prematurely releasing its payload (e.g., the medicament 110). When the system for targeted delivery to the duodenum 100 reaches the duodenum, the enteric coating 130 comprising a combination of the material degradable by the pH of the duodenum and the material digestible by a lipase can dissolve rapidly such that the needle delivery system 140 is released in the duodenum and such that release of the needle delivery system 140 results in engagement of the needles with the wall of the duodenum for release of the medicament 110. For example, the enteric coating 130 may degrade to a certain thickness or strength that can be overcome by force provided in a radially outward direction by a pre-loaded mechanical actuator of the needle delivery system 140. Alternatively, in some examples, at least some portion of the enteric coating 130 may degrade to facilitate the needle delivery system 140 being launched or ejected (e.g., in a longitudinal direction) to separate from an associated capsule, e.g., which may reduce a chance or risk that outward actuation of the needle delivery system 140 is obstructed or blocked by remnants of the capsule. Optionally, the enteric coating 130 includes a rigid material (e.g., EUDRAGIT® polymers (Evonik Industries AG, Essen Germany), shellac, carnauba wax, a candy coating, or any suitable rigid coating material). The rigid material can prevent water ingress into the medicament 110, thus protecting the medicament 110 and other layers of the enteric coating 130 from aqueous dissolution in the GI tract.

The system of the present disclosure is and may be in an orally administrable form (e.g., in the form of a pill or capsule). The enteric coating 130 is configured to protect the medicament 110 from stomach acid while allowing for release of the medicament 110 in a target portion of the gastrointestinal tract, e.g., the duodenum. The mucoadhesive layer 120 is configured to adhere to a wall of the duodenum, further ensuring the targeted delivery to the wall of the duodenum.

Figure 3:
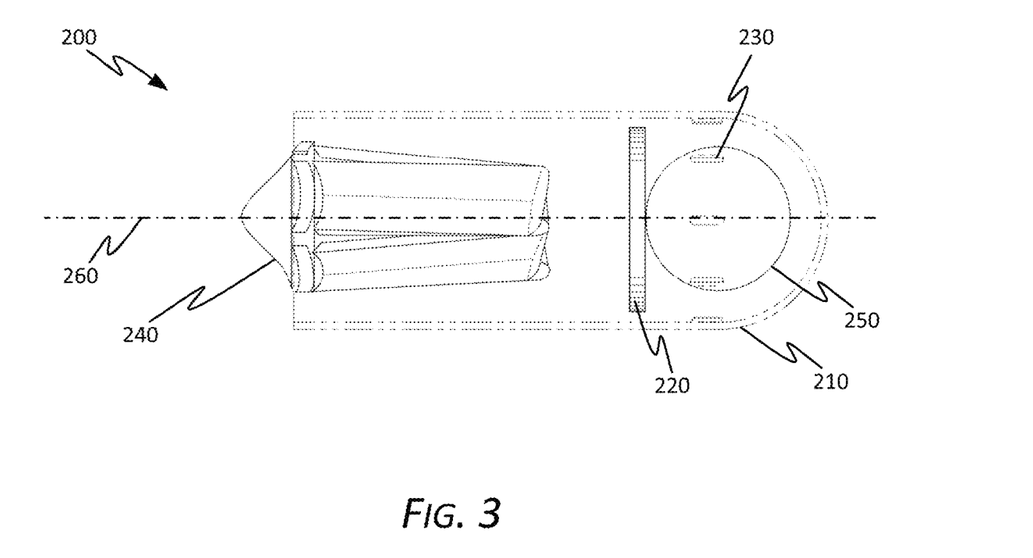
FIG. 3 shows a side view of a system for targeted delivery comprising a medicament-containing needle delivery system, a capsule, an enteric coating, and an expanding element to deploy the medicament-containing needle delivery system.

FIG. 3 shows a side view of a system 200 for targeted delivery comprising a medicament-containing needle delivery system, a capsule, and an expanding element to eject, launch, or deploy the medicament-containing needle delivery system. In this embodiment, a needle delivery system 240 is deployed or released so as to inject the medicament into the wall of duodenum or other relevant portion of the GI tract or other body lumen. The needle delivery system 240, along with the medicament, is encased by a capsule 240. For example, the capsule 240 may include the mucoadhesive layer 120 and/or the enteric coating 130 described above.

The capsule 210 defines a plurality of openings 230, e.g., at a first end of the system 200. The enteric coating may cover the openings 230 to seal the openings against fluid. The enteric coating may also cover and enclose the second end of the system 200 adjacent the needle delivery system 240. As the enteric coating is broken down or dissolved, the openings 230 are revealed or exposed and allow fluid to enter into the interior of the capsule 210.

Inside the capsule 210 of the system 200 is the needle delivery system 240, which may be the same as needle delivery system 140 described above. The needle delivery system 240 is stored within the system 200, e.g., near an opening where the needle delivery system 240 may be released or ejected from the capsule 210. Also within the capsule 210 is a piston 220 and an expanding element 250 that function to eject the needle delivery system 240 from the interior of the capsule 210, for example, along a longitudinal axis 260 of the capsule 210.

The piston 220 is a divider or wall that is capable of sliding along the length of the system 200. The piston 220 may include a single wall, may include a cup-shape, or additional features. Generally, the piston 220 forms a sufficient seal with the inside of the capsule 210 to act as a piston as the expanding element 250 expands to drive the needle delivery system 240 from the capsule 210.

As the enteric coating wears away or reveals the openings 230, fluid is allowed to enter the interior of the capsule 210 and come into contact with the expanding element 250. The expanding element 250 can include a super absorbent material that absorbs surrounding fluid and expands drastically, such as up to twenty times its original size. In some examples, the expanding element 250 expands to over twenty times its original size, such as up to four hundred times its size or greater. The expanding element 250 may include water-absorbing polymers such as hydrogels. Super absorbent polymers typically include cross-linked polymer networks of water-soluble components. In some examples, super absorbent polymers comprise ionic monomers. Super absorbent polymers are capable of absorbing and retaining fluids up to several hundred times their own weight, even when under pressure. Examples of super absorbent material may include sodium polyacrylate or other polyacrylates and silicones. In some examples, the super absorbent material may include starches, cellulose, gelatin, pectin, lignin, alginate, and other such materials. In some examples, the expanding element 250 may include other expanding elements such as springs, foams, elastic devices, or other such elements to expand volumetrically.

As the expanding element 250 absorbs fluid, it expands to many times its original weight and volume. The expansion of the expanding element 250 generates a force on the piston 220, causing the piston 220 to move leftward in the view shown in FIG. 3, e.g., along longitudinal axis 260. The movement of the piston 220 forces the needle delivery system 240 out of the capsule 210, where the needles can deploy to deliver medicament to a patient.

Figure 4:
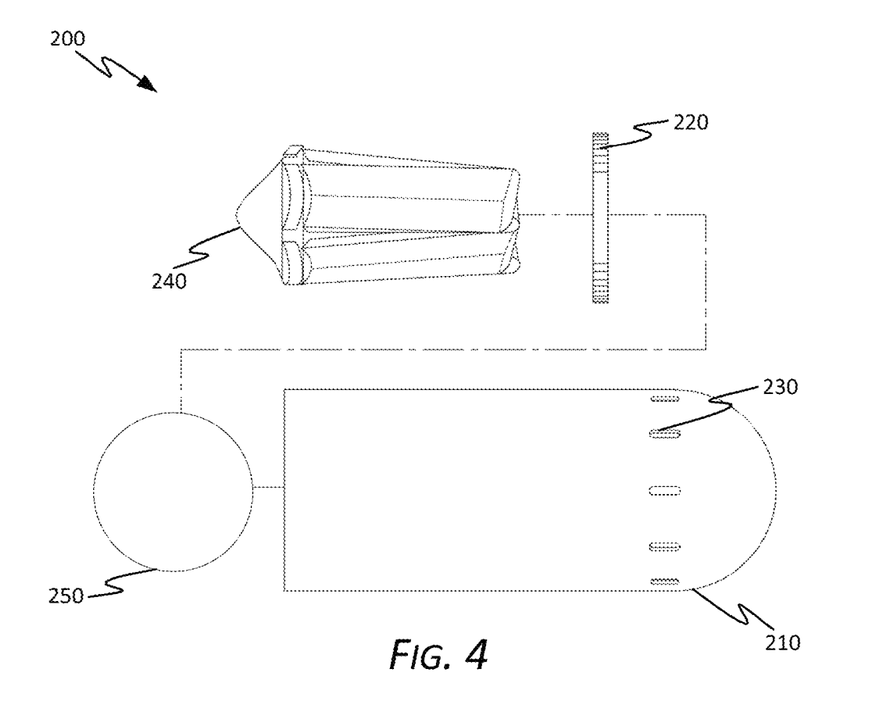
FIG. 4 shows an exploded view of a system for targeted delivery comprising a medicament-containing needle delivery system, a capsule, an enteric coating, and an expanding element to deploy the medicament-containing needle delivery system.

FIG. 4 shows features of the system 200 from FIG. 3 in an exploded view. When the system 200 is formed, the capsule 210 is loaded with an expanding element 250 (such as a mass of a super absorbent polymer). For example, the expanded element 250 can be positioned within or at the first end of the capsule 210 (e.g., the end including the openings 230). The piston 220 is installed inside adjacent the expanding element 250. A diameter or other dimension of the piston 220 may closely match or correspond to the interior of the capsule 210. Finally, the needle deployment system 240 is installed. The system 200 is coated with an enteric coating that seals openings 230 as well as the open end of the capsule 210. For example, in some aspects, the openings 230 correspond to areas formed of enteric coating that have a smaller thickness than surrounding areas of the enteric coating so that during dissolution, openings 230 will be produced and permit entry of fluid while surrounding areas of the enteric coating retain the expanding element 250 within the capsule 210.

Figure 5:
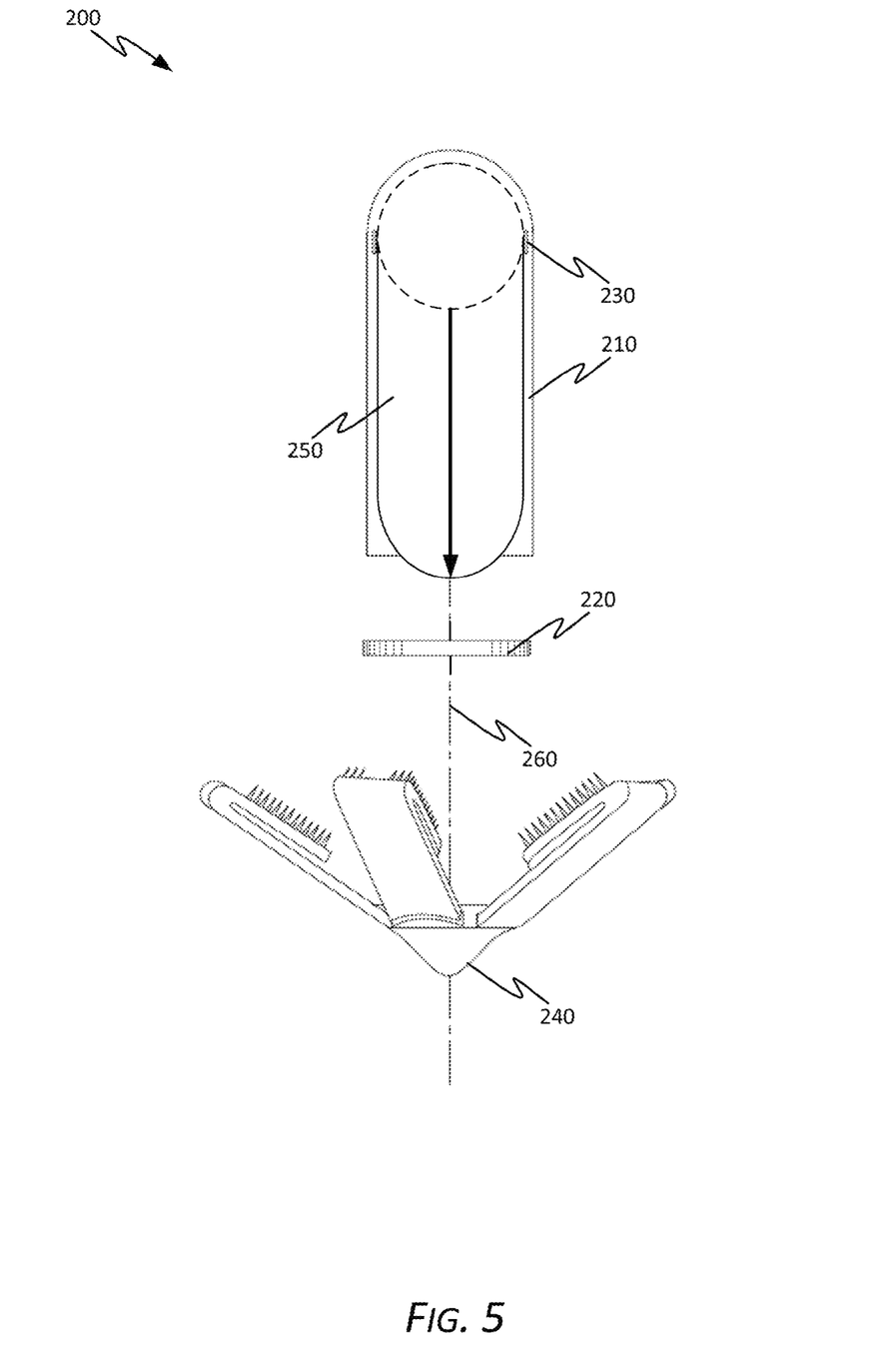
FIG. 5 shows a deployed system for targeted delivery comprising a medicament-containing needle delivery system.

FIG. 5 shows an example of a deployed state of features of the system 200 of FIGS. 3 and 4. As described above, the openings 230 enable fluid to transfer through the capsule 210 after an enteric coating has partially or totally broken down or otherwise been removed (e.g., in response to conditions in the duodenum). As the fluid enters the system 200, the fluid triggers expansion of the expanding element 250, such as by being absorbed by the expanding element 250. The expanding element 250 increases in volume as a result (e.g., expanding from the state shown in phantom lines to the state shown in solid lines) and forces the piston 220 to advance along the length of the system 200, e.g., along longitudinal axis 260. The piston 220 applies force to, and causes, a needle delivery system 240 to advance out of the capsule 210 of system 200 for delivery of medicament. For example, the needle delivery system 240 may be ejected, launched, or jettisoned along a longitudinal direction of the system 200 (e.g., along the longitudinal axis 260) to a position at which the needle delivery system 240 may expand radially or normal to the longitudinal axis 260 in order to engage tissue of the duodenum or other relevant body lumen.

As an illustrative example a subject may wish to take a dose of a biotherapeutic agent or other compound without resorting to a syringe injection, intravenous infusion, and potential accompanying discomfort or other concerns. To this end, the person may use a device according to this disclosure to provide the dosage. In this example, the device may be provided in pill or capsule form that the subject can swallow. Inside the pill or capsule are components capable of deploying within the body to effectively provide an internal injection, which may cause much smaller tissue disturbances and fewer systemic effects as compared to an external injection or infusion. As the pill or capsule reaches a target portion of the gastrointestinal tract (such as the duodenum), a specialized coating of the pill or capsule, such as the enteric coating described herein, has dissolved or degraded sufficiently to break apart and allow a mechanical actuator within the pill to expand outwardly. Multiple arrays of microneedles are arranged about the mechanical actuator and are driven by the outward expansion into engagement with surrounding tissue (e.g., tissue of a mucosal lining of the duodenum). The drug dose can be delivered to the tissue through the engaged microneedles, such as by flowing through the microneedles if hollow or by direct absorption if the drug is embedded in a dissolvable composition of the microneedles. After delivery of the dosage, the constituent parts of the device may biodegrade and avoid possible complications from trying to pass the device remains out of the body. Thus, the subject may use the device to administer an internal injection that may ultimately be less invasive, less arduous, and/or less troublesome to the subject than the alternative of using an external syringe or intravenous infusion. Furthermore, although the needle delivery system 240 is described and depicted as double hinged arms that are compressible toward and expandable away from a longitudinal axis 260, any other suitable alternative may be utilized, including, but not limited to a normally- or radially-expanding stent-like tube, an unwinding coil, an unfurling set of curved arms, a set of double-hinged arms that unfold relative to a central hub and then unfold again relative to parts connected to the hub, or a scissor-lift-like arrangement with centrally-hinged lateral columns that pop upright to an expanded state from a compressed state in which portions of the columns are hinged toward each other. Multiple arrays of microneedles are arranged about the mechanical actuator and are driven by the outward expansion into engagement with surrounding tissue (e.g., tissue of a mucosal lining of the duodenum).

In another aspect, a method is provided for making the system described herein. An exemplary embodiment includes the steps of providing a medicament (e.g., a capsule, a pill, and/or any other suitable orally administered medicament); coating the medicament with a mucoadhesive layer; and coating the medicament coated with the mucoadhesive layer with an enteric coating to provide a duodenum targeting medicament. As described herein, the enteric coating is configured to protect the medicament from stomach acid while allowing for release of the medicament in the duodenum.

Also provided herein is a method of making the system described herein wherein the system comprises a needle delivery system. The method includes providing a medicament associated with a needle delivery system (e.g., a medicament contained in a needle delivery system where the needles are configured to pass the medicament into the wall of the duodenum, a medicament needle configured to enter the wall of the duodenum and dissolve into the wall of the duodenum, a needle configured to push a medicament into the wall of the duodenum, and/or any combination thereof); coating the medicament-associated needle delivery system with a mucoadhesive layer; and coating the medicament-associated needle delivery system coated with the mucoadhesive layer with an enteric coating to provide a duodenum targeting medicament with a needle delivery system.

Also provided herein is a method of making the system described herein wherein the system comprises a piston and expanding material for driving a needle delivery system. The method includes providing a needle delivery system, a piston, and an expanding material (such as a super absorbent material); and positioning the expanding material, the piston, and the needle delivery system within a capsule (e.g., by introducing into a pre-made capsule formed of a mucoadhesive material and/or an enteric coating, or by applying a coating to a subassembly of the needle delivery system, the piston, and the superabsorbent material, where the coating includes an enteric coating or a mucoadhesive layer that is in turn coated by an enteric coating).

The system for targeted delivery to the duodenum described herein may be used for the delivery of any suitable medicament to the gastrointestinal tract of a mammal, such as a human, canine, bovine or porcine intestinal tract. Characteristics of the system, the needle delivery device, and the medicament may be tailored for the particular mammal(s) receiving the medicament and the desired purpose. For example, in embodiments of the device employing various biodegradable materials, the pH under which those materials will degrade may be selected based on the pH of the target portion of the GI tract of the chosen mammal.

After release of the medicament to the subject, components of the system may be absorbed by the subject (e.g., based on use of biodegradable materials) and/or excreted by the subject. Thus, portions of the mucoadhesive layer, an enteric coating, or needle delivery system may further degrade in the GI tract or be excreted by the subject.

Enteric coatings, as described herein, provide a protective seal over at least a portion of the surface of the system such that digestive fluids do not enter the system interior or release the medicament until the system has reached the small intestine. The enteric coating may be configured to degrade in response to compressive forces applied by a peristaltic contraction within the small intestine or to degrade after a certain period of time has elapsed.

Another aspect of the invention provides methods for the delivery of medicaments into the duodenum using embodiments of the swallowable medicament delivery system. The types and amounts of the medicament delivered can be titrated for the subject's weight, age, or other parameters. Embodiments of the swallowable medicament delivery device can be used to deliver a one or a plurality of medicaments. In some cases, such embodiments allow a subject to forgo the necessity of having to take multiple separate doses of one or more medicaments. Accordingly, such embodiments facilitate delivery of multiple medicaments at about the same time. Due to differences in their size, shape, materials and functionalized receptors, different types of medicaments can be absorbed through the intestinal wall of the duodenum at different rates. Further, the various embodiments of the swallowable delivery device provide a means for delivering medicaments to the bloodstream via the GI tract that might otherwise require injection due to chemical breakdown in the stomach.

A subject receiving the delivery system may have a disease, illness, disorder, injury, condition or impairment necessitating the medicament. A person of skill in the art can determine the proper medicament(s) and dosage form depending on a number of factors, including the type and severity of the disease, illness, disorder, injury, condition or impairment.

Illustrative Enteric Coatings

In some cases, the material digestible by a lipase comprises a wax material (e.g., coconut oil, bee's wax, or any suitable waxy material) and the material degradable by a pH of the duodenum comprises a polymer (e.g., the polymer comprises gelatin paper or sheets, rice paper or sheets, polylactic acid, nylon, polyester, PVA (polyvinyl alcohol), or other corn-based polymers). In certain aspects, the enteric coating encasing the medicament does not degrade in a mammal stomach (e.g., a human stomach). In certain cases, the enteric coating encasing the medicament can dissolve in less than one minute when the medicament arrives at the duodenum. For example, the enteric coating encasing the medicament can dissolve in less than about 1 second, less than about 2 seconds, less than about 3 seconds, less than about 4 seconds, less than about 5 seconds, less than about 6 seconds, less than about 7 seconds, less than about 8 seconds, less than about 9 seconds, less than about 10 seconds, less than about 11 seconds, less than about 12 seconds, less than about 13 seconds, less than about 14 seconds, less than about 15 seconds, less than about 16 seconds, less than about 17 seconds, less than about 18 seconds, less than about 19 seconds, less than about 20 seconds, less than about 21 seconds, less than about 22 seconds, less than about 23 seconds, less than about 24 seconds, less than about 25 seconds, less than about 26 seconds, less than about 27 seconds, less than about 28 seconds, less than about 29 seconds, less than about 30 seconds, less than about 31 seconds, less than about 32 seconds, less than about 33 seconds, less than about 34 seconds, less than about 35 seconds, less than about 36 seconds, less than about 37 seconds, less than about 38 seconds, less than about 39 seconds, less than about 40 seconds, less than about 41 seconds, less than about 42 seconds, less than about 43 seconds, less than about 44 seconds, less than about 45 seconds, less than about 46 seconds, less than about 47 seconds, less than about 48 seconds, less than about 49 seconds, less than about 50 seconds, less than about 51 seconds, less than about 52 seconds, less than about 53 seconds, less than about 54 seconds, less than about 55 seconds, less than about 56 seconds, less than about 57 seconds, less than about 58 seconds, less than about 59 seconds, or less than about one minute. Optionally, the enteric coating encasing the medicament degrades at a rate of from 5 $(mg/cm^3)/min$ to 26 $(mg/cm^3)/min$ (e.g., a rate of from 5.1 $(mg/cm^3)/min$ to 25.9 $(mg/cm^3)/min$, from 6 $(mg/cm^3)/min$ to 24 $(mg/cm^3)/min$, from 8 $(mg/cm^3)/min$ to 22 $(mg/cm^3)/min$, from 10 $(mg/cm^3)/min$ to 20 $(mg/cm^3)/min$, or from 5.9 $(mg/cm^3)/min$ to 25.1 $(mg/cm^3)/min$). For example, the enteric coating encasing the medicament degrades at a rate of 5 $(mg/cm^3)/min$, 5.1 $(mg/cm^3m)/min$, 5.2 $(mg/cm^3m)/min$, 5.3 $(mg/cm^3m)/min$, 5.4 $(mg/cm^3)/min$, 5.5 $(mg/cm^3)/min$, 5.6 $(mg/cm^3)/min$, 5.7 $(mg/cm^3)/min$, 5.8 $(mg/cm^3)/min$, 5.9 $(mg/cm^3)/min$, 6 $(mg/cm^3)/min$, 6.1 $(mg/cm^3)/min$, 6.2 $(mg/cm^3)/min$, 6.3 $(mg/cm^3)/min$, 6.4 $(mg/cm^3)/min$, 6.5 $(mg/cm^3)/min$, 6.6 $(mg/cm^3)/min$, 6.7 $(mg/cm^3)/min$, 6.8 $(mg/cm^3)/min$, 6.9 $(mg/cm^3)/min$, 7 $(mg/cm^3)/min$, 7.1 $(mg/cm^3)/min$, 7.2 $(mg/cm^3)/min$, 7.3 $(mg/cm^3)/min$, 7.4 $(mg/cm^3)/min$, 7.5 $(mg/cm^3)/min$, 7.6 $(mg/cm^3)/min$, 7.7 $(mg/cm^3)/min$, 7.8 $(mg/cm^3)/min$, 7.9 $(mg/cm^3)/min$, 8 $(mg/cm^3)/min$, 8.1 $(mg/cm^3)/min$, 8.2 $(mg/cm^3)/min$, 8.3 $(mg/cm^3)/min$, 8.4 $(mg/cm^3)/min$, 8.5 $(mg/cm^3)/min$, 8.6 $(mg/cm^3)/min$, 8.7 $(mg/cm^3)/min$, 8.8 $(mg/cm^3)/min$, 8.9 $(mg/cm^3)/min$, 9 $(mg/cm^3)/min$, 9.1 $(mg/cm^3)/min$, 9.2 $(mg/cm^3)/min$, 9.3 $(mg/cm^3)/min$, 9.4 $(mg/cm^3)/min$, 9.5 $(mg/cm^3)/min$, 9.6 $(mg/cm^3)/min$, 9.7 $(mg/cm^3)/min$, 9.8 $(mg/cm^3)/min$, 9.9 $(mg/cm^3)/min$, 10 $(mg/cm^3)/min$, 10.1 $(mg/cm^3)/min$, 10.2 $(mg/cm^3)/min$, 10.3 $(mg/cm^3)/min$, 10.4 $(mg/cm^3)/min$, 10.5 $(mg/cm^3)/min$, 10.6 $(mg/cm^3)/min$, 10.7 $(mg/cm^3)/min$, 10.8 $(mg/cm^3)/min$, 10.9 $(mg/cm^3)/min$, 11 $(mg/cm^3)/min$, 11.1 $(mg/cm^3)/min$, 11.2 $(mg/cm^3)/min$, 11.3 $(mg/cm^3)/min$, 11.4 $(mg/cm^3)/min$, 11.5 $(mg/cm^3)/min$, 11.6 $(mg/cm^3)/min$, 11.7 $(mg/cm^3)/min$, 11.8 $(mg/cm^3)/min$, 11.9 $(mg/cm^3)/min$, 12 $(mg/cm^3)/min$, 12.1 $(mg/cm^3)/min$, 12.2 $(mg/cm^3)/min$, 12.3 $(mg/cm^3)/min$, 12.4 $(mg/cm^3)/min$, 12.5 $(mg/cm^3)/min$, 12.6 $(mg/cm^3)/min$, 12.7 $(mg/cm^3)/min$, 12.8 $(mg/cm^3)/min$, 12.9 $(mg/cm^3)/min$, 13 $(mg/cm^3)/min$, 13.1 $(mg/cm^3)/min$, 13.2 $(mg/cm^3)/min$, 13.3 $(mg/cm^3)/min$, 13.4 $(mg/cm^3)/min$, 13.5 $(mg/cm^3)/min$, 13.6 $(mg/cm^3)/min$, 13.7 $(mg/cm^3)/min$, 13.8 $(mg/cm^3)/min$, 13.9 $(mg/cm^3)/min$, 14 $(mg/cm^3)/min$, 14.1 $(mg/cm^3)/min$, 14.2 $(mg/cm^3)/min$, 14.3 $(mg/cm^3)/min$, 14.4 $(mg/cm^3)/min$, 14.5 $(mg/cm^3)/min$, 14.6 $(mg/cm^3)/min$, 14.7 $(mg/cm^3)/min$, 14.8 $(mg/cm^3)/min$, 14.9 $(mg/cm^3)/min$, 15 $(mg/cm^3)/min$, 15.1 $(mg/cm^3)/min$, 15.2 $(mg/cm^3)/min$, 15.3 $(mg/cm^3)/min$, 15.4 $(mg/cm^3)/min$, 15.5 $(mg/cm^3)/min$, 15.6 $(mg/cm^3)/min$, 15.7 $(mg/cm^3)/min$, 15.8 $(mg/cm^3)/min$, 15.9 $(mg/cm^3)/min$, 16 $(mg/cm^3)/min$, 16.1 $(mg/cm^3)/min$, 16.2 $(mg/cm^3)/min$, 16.3 $(mg/cm^3)/min$, 16.4 $(mg/cm^3)/min$, 16.5 $(mg/cm^3)/min$, 16.6 $(mg/cm^3)/min$, 16.7 $(mg/cm^3)/min$, 16.8 $(mg/cm^3)/min$, 16.9 $(mg/cm^3)/min$, 17 $(mg/cm^3)/min$, 17.1 $(mg/cm^3)/min$, 17.2 $(mg/cm^3)/min$, 17.3 $(mg/cm^3)/min$, 17.4 $(mg/cm^3)/min$, 17.5 $(mg/cm^3)/min$, 17.6 $(mg/cm^3)/min$, 17.7 $(mg/cm^3)/min$, 17.8 $(mg/cm^3)/min$, 17.9 $(mg/cm^3)/min$, 18 $(mg/cm^3)/min$, 18.1 $(mg/cm^3)/min$, 18.2 $(mg/cm^3)/min$, 18.3 $(mg/cm^3)/min$, 18.4 $(mg/cm^3)/min$, 18.5 $(mg/cm^3)/min$, 18.6 $(mg/cm^3)/min$, 18.7 $(mg/cm^3)/min$, 18.8 $(mg/cm^3)/min$, 18.9 $(mg/cm^3)/min$, 19 $(mg/cm^3)/min$, 19.1 $(mg/cm^3)/min$, 19.2 $(mg/cm^3)/min$, 19.3 $(mg/cm^3)/min$, 19.4 $(mg/cm^3)/min$, 19.5 $(mg/cm^3)/min$, 19.6 $(mg/cm^3)/min$, 19.7 $(mg/cm^3)/min$, 19.8 $(mg/cm^3)/min$, 19.9 $(mg/cm^3)/min$, 20 $(mg/cm^3)/min$, 20.1 $(mg/cm^3)/min$, 20.2 $(mg/cm^3)/min$, 20.3 $(mg/cm^3)/min$, 20.4 $(mg/cm^3)/min$, 20.5 $(mg/cm^3)/min$, 20.6 $(mg/cm^3)/min$, 20.7 $(mg/cm^3)/min$, 20.8 $(mg/cm^3)/min$, 20.9 $(mg/cm^3)/min$, 21 $(mg/cm^3)/min$, 21.1 $(mg/cm^3)/min$, 21.2 $(mg/cm^3)/min$, 21.3 $(mg/cm^3)/min$, 21.4 $(mg/cm^3)/min$, 21.5 $(mg/cm^3)/min$, 21.6 $(mg/cm^3)/min$, 21.7 $(mg/cm^3)/min$, 21.8 $(mg/cm^3)/min$, 21.9 $(mg/cm^3)/min$, 22 $(mg/cm^3)/min$, 22.1 $(mg/cm^3)/min$, 22.2 $(mg/cm^3)/min$, 22.3 $(mg/cm^3)/min$, 22.4 $(mg/cm^3)/min$, 22.5 $(mg/cm^3)/min$, 22.6 $(mg/cm^3)/min$, 22.7 $(mg/cm^3)/min$, 22.8 $(mg/cm^3)/min$, 22.9 $(mg/cm^3)/min$, 23 $(mg/cm^3)/min$, 23.1 $(mg/cm^3)/min$, 23.2 $(mg/cm^3)/min$, 23.3 $(mg/cm^3)/min$, 23.4 $(mg/cm^3)/min$, 23.5 $(mg/cm^3)/min$, 23.6 $(mg/cm^3)/min$, 23.7 $(mg/cm^3)/min$, 23.8 $(mg/cm^3)/min$, 23.9 $(mg/cm^3)/min$, 24 $(mg/cm^3)/min$, 24.1 $(mg/cm^3)/min$, 24.2 $(mg/cm^3)/min$, 24.3 $(mg/cm^3)/min$, 24.4 $(mg/cm^3)/min$, 24.5 $(mg/cm^3)/min$, 24.6 $(mg/cm^3)/min$, 24.7 $(mg/cm^3)/min$, 24.8 $(mg/cm^3)/min$, 24.9 $(mg/cm^3)/min$, 25 $(mg/cm^3)/min$, 25.1 $(mg/cm^3)/min$, 25.2 $(mg/cm^3)/min$, 25.3 $(mg/cm^3)/min$, 25.4 $(mg/cm^3)/min$, 25.5 $(mg/cm^3)/min$, 25.6 $(mg/cm^3)/min$, 25.7 $(mg/cm^3)/min$, 25.8 $(mg/cm^3)/min$, 25.9 $(mg/cm^3)/min$, or 26 $(mg/cm^3)/min$.

In certain embodiments, the enteric coating includes an outer layer that is the lipase-digestible material. For example, the lipase-digestible material can partially or completely cover the targeted delivery system for targeting the duodenum. For example, the system for targeting delivery to a wall of the duodenum can be 100% coated by the lipase-digestible material system for targeted delivery to a wall of the duodenum, at least 99% coated by the lipase-digestible material, at least 95% coated by the lipase-digestible material, at least 90% coated by the lipase-digestible material, at least 85% coated by the lipase-digestible material, at least 80% coated by the lipase-digestible material, at least 75% coated by the lipase-digestible material, at least 70% coated by the lipase-digestible material, at least 65% coated by the lipase-digestible material, at least 60% coated by the lipase-digestible material, at least 55% coated by the lipase-digestible material, at least 50% coated by the lipase-digestible material, at least 45% coated by the lipase-digestible material, at least 40% coated by the lipase-digestible material, at least 35% coated by the lipase-digestible material, at least 30% coated by the lipase-digestible material, at least 25% coated by the lipase-digestible material, at least 20% coated by the lipase-digestible material, at least 15% coated by the lipase-digestible material, at least 10% coated by the lipase-digestible material, at least 5% coated by the lipase-digestible material, or at least 1% coated by the lipase-digestible material.

The enteric coating optionally further includes a rigid material (e.g., EUDRAGIT® polymers (Evonik Industries AG, Essen Germany), shellac, carnauba wax, a candy coating, or any suitable rigid coating material). Optionally, the rigid material is coated over the waxy material, such that the rigid material encapsulates and is external to the waxy layer, which lies between the medicament and the rigid material. The rigid material can prevent or delay water ingress into the medicament, thus protecting the medicament and other layers of the enteric coating from aqueous dissolution in the GI tract or dissolution before reaching the duodenum.

In certain embodiments, the enteric coating includes an second (inner or outer) layer that is coated by the lipase-digestible material. The second layer is optionally a polymer layer. Thus, the polymer layer can be encased by the lipase-digestible material, such that the polymer layer is exposed to acids in the duodenum after the lipase-digestible material is degraded. For example, the system for targeted delivery to a wall of the duodenum can be 100% coated by the polymer, can be at least 99% coated by the polymer, at least 95% coated by the polymer, at least 90% coated by the polymer, at least 85% coated by the polymer, at least 80% coated by the polymer, at least 75% coated by the polymer, at least 70% coated by the polymer, at least 65% coated by the polymer, at least 60% coated by the polymer, at least 55% coated by the polymer, at least 50% coated by the polymer, at least 45% coated by the polymer, at least 40% coated by the polymer, at least 35% coated by the polymer, at least 30% coated by the polymer, at least 25% coated by the polymer, at least 20% coated by the polymer, at least 15% coated by the polymer, at least 10% coated by the polymer, at least 5% coated by the polymer, or at least 1% coated by the polymer. Further, the polymer layer can be 100% coated by the lipase-digestible material, at least 99% coated by the lipase-digestible material, at least 95% coated by the lipase-digestible material, at least 90% coated by the lipase-digestible material, at least 85% coated by the lipase-digestible material, at least 80% coated by the lipase-digestible material, at least 75% coated by the lipase-digestible material, at least 70% coated by the lipase-digestible material, at least 65% coated by the lipase-digestible material, at least 60% coated by the lipase-digestible material, at least 55% coated by the lipase-digestible material, at least 50% coated by the lipase-digestible material, at least 45% coated by the lipase-digestible material, at least 40% coated by the lipase-digestible material, at least 35% coated by the lipase-digestible material, at least 30% coated by the lipase-digestible material, at least 25% coated by the lipase-digestible material, at least 20% coated by the lipase-digestible material, at least 15% coated by the lipase-digestible material, at least 10% coated by the lipase-digestible material, at least 5% coated by the lipase-digestible material, or at least 1% coated by the lipase-digestible material.

In some embodiments, the enteric coating is a combination of the lipase-digestible material and the polymer. Accordingly, the enteric coating can be a single layer comprising both polymer and lipase digestible components, wherein the enteric coating encases the system for targeted delivery to a wall of the duodenum configured to degrade when the system for targeted delivery to a wall of the duodenum reaches the duodenum. In some cases, the lipase-digestible material and the polymer can be present on the system for targeted delivery to a wall of the duodenum in a ratio of 1:1, 2:1, 3:1, 4:1, 5:1, 6:1, 7:1, 8:1, 9:1, 10:1, 20:1, 30:1, 40:1, 50:1, 60:1, 70:1, 80:1, 90:1, 99:1, or anywhere in between, and vice versa.

In certain embodiments, the enteric coating encasing the medicament or medicament-containing needle delivery system degrades to expose the mucoadhesive layer and to allow the mucoadhesive layer to attach the system for targeted delivery to a wall of the duodenum. Accordingly, after the enteric coating degrades, the system for targeted delivery to a wall of the duodenum can adhere to the wall of the duodenum. When adhered to the wall of the duodenum, the system for targeted delivery to a wall of the duodenum and the medicament contained therein can remain in the duodenum until the medicament is fully adsorbed or injected into the wall of the duodenum.

In certain aspects, the enteric coating encasing the medicament degrades to expose the medicament or medicament-containing needle delivery system, and the medicament is absorbed by or injected into the wall of the duodenum. As such, once the medicament is exposed to the acids present in the duodenum, the medicament is positioned for rapid adsorption through the wall of the duodenum and into the subject's blood stream.

In certain aspects, targeting moieties can be added to the system for targeting delivery. By way of example, the targeting moieties can comprise a moiety that binds a tumor antigen (e.g., a tumor antigen in the GI tract of a subject).

The medicament in the system for targeted delivery may comprise a biomarkers, chemoluminescent markers, photoluminescent markers, or any combination thereof. Such markers can be used for diagnostic purposes or for determining the level of absorbed or unabsorbed medicament.

Illustrative Swallowable Devices

In certain examples, the system for targeted delivery to a wall of the duodenum is a swallowable device having a capsule containing one or a plurality of medicaments. The capsule is optionally sized to pass through a lumen of a gastrointestinal tract. The capsule can be coated with at least the enteric coating described herein. In other examples, the capsule can be coated with the mucoadhesive layer and the enteric coating described above. Thus, the system for targeted delivery to a wall of the duodenum can be configured to adhere to a target portion of the GI tract, e.g., the wall of the duodenum. Alternatively, the target portion of the GI tract could be the jejunum, ileum, large intestine, stomach, or any suitable portion of the GI tract. Delivery of the medicament may occur in response to a chemical condition in the duodenum. For example, delivery may occur upon exposure to chemical conditions in the duodenum such as pH, such as upon exposure to a selected pH in the duodenum, e.g., 7.0, 7.1, 7.2, 7.3, 7.4, 7.5, 7.6 8.0 or greater. In some examples, delivery may occur in a pH range from 7.0 to 7.5. In other examples, delivery may occur in response to a mechanical or electrochemical stimulus. In still further examples, delivery may occur in response to a stimulus remote from the swallowable device. In some examples, delivery may be actuated by enabling fluid to contact an expanding material, such as a super absorbent material, causing the expanding material to swell and deliver the needle delivery system and medicament.

One or more embodiments of the system for targeted delivery to a wall of the duodenum described herein can be used for the delivery of one or a plurality of medicaments or medicament-containing needle delivery systems to the body. The medicament can be a therapeutic agent (e.g., a biotherapeutic agent) or can be a diagnostic agent. The medicament can be molecules, compounds or other substances ill-suited for traditional oral delivery.

Embodiments of the system for targeted delivery to a wall of the duodenum allow the one or more medicaments to be delivered to or into the wall of the duodenum (or other targeted delivery site). Optionally, the medicament is absorbed into the blood stream with minimal or no loss of activity, affinity or specificity.

Further, embodiments of the system for targeted delivery optionally provide for the delivery of multiple types of medicaments in a single dose or capsule. Thus, a combination of medicaments or a medicament and another agent, such as a contrast agent, fluorophore, enzyme, reactant, etc., can delivered concurrently. Such timing may be important for the additional agent to provide some assistance or benefit to the action of the medicament. Additionally, eliminating the need to take multiple doses of medicaments may be beneficial to subject compliance and timing.

By way of example, the system can be a capsule that includes a medicament that is preferably delivered to the duodenum, e.g., a human duodenum. The capsule can be sized to pass through the GI tract of the subject receiving it. In some examples, the capsule can meet criteria for being classified as a 000 capsule as known be persons of skill in the art, although other standardized or custom types of capsule may be used. The capsule may be sized to facilitate functioning in a particular body portion. For example, a capsule of 000 type may have an outer surface with an overall length of approximately 26.14 mm (millimeters) and a body diameter of 9.55 mm, which dimensions may be suitable for operation or use in a portion of the GI tract corresponding to the duodenum (e.g., based on a human duodenum typically ranging from between 25 mm when fully open and nearly 0 mm when fully closed or constricted during peristalsis). In some examples, a length of the capsule being greater than or approximately equal to a largest expected diameter or other cross-sectional dimension of the body lumen may pre-dispose the capsule toward a predetermined orientation in which the system is suitably aligned for expanding to engage with the surrounding tissue (e.g., with lengths of the capsule and body lumen aligned so the device can expand along diameters of the device and body lumen).

The inner surface can bound or otherwise define an interior volume of the capsule, e.g., in which the system and/or respective components may be disposed. The inner surface may be separated from the outer surface by a wall thickness, e.g., such that dimensions between respective portions of the inner surface may be reduced by two times the wall thickness from dimensions of the outer surface. As an illustrative example, a capsule of 000 type may have a wall thickness of 0.11 mm such that the interior volume has overall internal length of approximately 25.92 mm (millimeters) in length and an internal body diameter of 9.33 mm.

Medicaments in the system provided herein can include, but are not limited to biotherapeutics (e.g., peptides, monoclonal antibodies (or portions thereof), and/or nucleic acids. Traditionally, biotherapeutics have been ineffective to deliver orally because they are at least 100 times in magnitude too large compared to recognized size limits for orally deliverable drugs. For example, where a biotherapeutic may be approximately 150 kilodaltons (kDa) in size, an orally deliverable drug may be approximately 0.5 kDa in size. In comparison to traditional small molecule therapeutics that can be orally delivered and absorbed during the process of digestion, biotherapeutics often bring better efficacy and specificity but at the cost of drug delivery challenges. In essence, the large size of these biotherapeutics has conventionally necessitated frequent delivery through needle injections, such as through a handheld syringe or an intravenous catheter commonly referred to as an IV. However, injections or infusions may contribute to patient compliance challenges, high administration costs by trained medical staff, needlestick contamination, needle phobia, and a heightened risk of systemic infection.

Illustrative Methods

By way of example, provided herein is a method of making the system for targeted delivery. As described previously, the medicament can be encased in a digestible waxy material 210 as shown in FIG. 2. The digestible waxy material 210 can be used to maintain an expanding element in a compressed position until the digestible waxy material is digested in the duodenum. Encasing the medicament in the digestible waxy material can be performed using an injection molding technique. As such, the medicament can be placed into a polymer (e.g., HPMCAS) or a gelatin shell and closed, serving as a mold. The digestible waxy material can be injected into the mold encasing the expanding element in the digestible waxy material. In certain embodiments, the encasing process is performed at a temperature of from −20° C. to +25° C. (e.g., from −15° C. to +15° C., from −10° C. to +10° C., from −20° C. to 0° C., or from −20° C. to −5° C.). For example, the encasing process can be performed at a temperature of about −20° C., about −19° C., about −18° C., about −17° C., about −16° C., about −15° C., about −14° C., about −13° C., about −12° C., about −11° C., about −10° C., about −9° C., about −8° C., about −7° C., about −6° C., about −5° C., about −4° C., about −3° C., about −2° C., about −1° C., about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., or about 25° C. Encasing the medicament at a temperature of from −20° C. to +25° C. can prevent creep that can occur while encasing the medicament.

Optionally, such a method can comprise providing a medicament as described herein; coating the medicament with a mucoadhesive layer or injecting the medicament into a mucoadhesive layer to provide a mucoadhesive-coated medicament; at least partially coating the mucoadhesive-coated medicament with at least a material degradable by a pH in a duodenum; and at least partially coating the mucoadhesive-coated medicament with at least a material digestible by a lipase.

The material degradable by a pH in a duodenum is optionally a polymer and the material digestible by a lipase is a wax material. Optionally the material degradable by a pH and a material digestible by a lipase are applied concurrently to coat the mucoadhesive-coated medicament. In such case, the ratio of material degradable by a pH to material digestible by a lipase applied to mucoadhesive-coated medicament is a 1:1 ratio, a 0.6 to 0.4 ratio, a 0.4 to 0.6 ratio a 0.7 to 0.3 ratio, a 0.3 to 0.7 ratio.

Also provided herein is a method of targeting delivery of a medicament to a duodenum, comprising administering to a subject a targeted delivery system described herein or a targeted delivery system made by the methods described herein. Optionally, the targeted delivery system is administered to the subject orally.

As used below, any reference to a series of examples is to be understood as a reference to each of those examples disjunctively (e.g., "Examples 1-4" is to be understood as "Examples 1, 2, 3, or 4").

Example 1 is a system for targeted delivery of a medicament to a gastrointestinal (GI) tract of a subject, comprising: (a) a medicament; (b) a mucoadhesive layer at least partially surrounding the medicament; and (c) an enteric coating encasing the medicament and mucoadhesive layer, wherein the enteric coating comprises a material degradable by a pH of the GI tract and a material digestible by a lipase.

Example 2 is the system for targeted delivery of a medicament of example(s) 1, wherein the enteric coating further comprises a rigid material layer.

Example 3 is the system for targeted delivery of a medicament of example(s) 1 or 2, wherein the material digestible by a lipase comprises a wax material.

Example 4 is the system for targeted delivery of a medicament of any one of example(s) 1-3, wherein the material degradable by a pH of the GI tract comprises a polymer.

Example 5 is the system for targeted delivery of a medicament of example(s) 3, wherein the polymer comprises gelatin paper or sheets, rice paper or sheets, polylactic acid, nylon, polyester, PVA (polyvinyl alcohol), or corn-based polymers.

Example 6 is the system for targeted delivery of a medicament of any one of example(s) 1-5, wherein the enteric coating encasing the medicament and mucoadhesive layer is configured to degrade in a human duodenum.

Example 7 is the system for targeted delivery of a medicament of any one of example(s) 1-6, wherein the enteric coating encasing the medicament and mucoadhesive layer is configured to not degrade in a human stomach.

Example 8 is the system for targeted delivery of a medicament of any one of example(s) 1-7, wherein the enteric coating encasing the medicament is configured to degrade in less than one minute in the duodenum of the subject.

Example 9 is the system for targeted delivery of a medicament of any one of example(s) 1-8, wherein the mucoadhesive layer is selected to adhere to a wall of the GI tract of the subject.

Example 10 is the system for targeted delivery of a medicament of any one of example(s) 1-9, wherein the enteric coating is configured to expose the mucoadhesive layer and the medicament to the wall of the GI tract.

Example 11 is the system for targeted delivery of a medicament of any one of example(s) 1-10, further comprising: (d) a medicament needle system for delivering the medicament to the GI tract; (e) an expanding element expandable in response to absorbing fluid for driving the medicament and medicament needle system out of the mucoadhesive layer.

Example 12 is a method of making a system for targeted delivery of a medicament to a gastrointestinal (GI) tract of a subject, comprising: (a) providing a medicament; (b) at least partially coating the medicament with a mucoadhesive layer to provide a mucoadhesive-coated medicament; (c) at least partially coating the mucoadhesive-coated medicament with a material degradable by a pH of the GI tract; and (d) at least partially coating the mucoadhesive-coated medicament with a material digestible by a lipase.

Example 13 is the method of example(s) 12, wherein steps (c) and (d) are performed concurrently.

Example 14 is the method of example(s) 13, wherein steps (c) and (d) comprises coating the mucoadhesive-coated medicament with a composition comprising the material degradable by a pH of the GI tract and the material digestible by a lipase in a ratio of 1:1, 0.6:0.4, 0.4:0.6, 0.7:0.3, 0.3:0.7.

Example 15 is the method of example(s) 12, wherein steps (c) and (d) are performed separately.

Example 16 is the method of example(s) 15, wherein steps (c) and (d) result in a 1:1, 0.6:0.4, 0.4:0.6, 0.7:0.3, 0.3:0.7 ratio of the material degradable by a pH of the GI tract and the material digestible by a lipase coating the mucoadhesive-coated medicament.

Example 17 is the method of any one of example(s)s 12-16, wherein the material degradable by a pH of the GI tract comprises a polymer.

Example 18 is the method of any one of example(s)s 12-17, wherein the material digestible by a lipase comprises a wax material.

Example 19 is the method of any one of example(s)s 12-18, further comprising providing an expanding material and wherein providing the medicament comprises providing a needle delivery system, the expanding material expandable to deploy the needle delivery system out of the mucoadhesive layer.

Example 20 is a method of administering a medicament directly to the gastrointestinal (GI) tract of a subject, administering to the subject the system of any one of example(s)s 1-11 or made by the method of any one of example(s)s 12-19.

Example 21 is the method of example(s) 20, wherein the system is administered orally to the subject.

Example 22 is the method of example(s) 20 or 21, wherein the medicament is administered selectively to the GI tract of the subject.

Example 23 is the method of example(s) 22, wherein the medicament is administered selectively to the duodenum of the subject.

Example 24 is a system for targeted delivery of a medicament to a gastrointestinal (GI) tract of a subject, comprising: (a) a medicament; (b) a medicament needle system for delivering the medicament to the GI tract; (c) a capsule at least partially encasing the medicament needle system and including or coated by an enteric coating; and (d) an expanding element expandable in response to absorbing fluid for driving the medicament and medicament needle system out of the capsule.

Example 25 is the system of example(s) 24, wherein the capsule at least partially surrounds the medicament and the capsule defines a first opening and a second opening, the first opening adjacent the medicament needle system and the second opening adjacent the expanding element.

Example 26 is the system of example(s) 25, wherein the enteric coating closes the first opening and the second opening.

Example 27 is the system of any one of example(s) 24-26, wherein the expanding element comprises a super absorbent material.

Example 28 is the system of example(s) 27, wherein the super absorbent material comprises polyacrylate.

Example 29 is the system of example(s) 27, wherein the super absorbent material is bio-compatible and configured to expand in volume as fluid is absorbed by the super absorbent material.

Example 30 is the system of example(s) 27-29, wherein the expanding element further comprises a piston and wherein the super absorbent material and the medicament needle system are on opposing sides of the piston.

Example 31 is the system of any one of example(s) 24-30, wherein the enteric coating comprises a material degradable by a pH of the GI tract and a material digestible by a lipase.

Example 32 is a method of making a system for targeted delivery of a medicament to a gastrointestinal (GI) tract of a subject, comprising: (a) providing a medicament; (b) providing an expanding material; and (c) at least partially enclosing the medicament and the expanding material with a capsule.

Example 33 is the method of example(s) 32, wherein: (a) the medicament comprises an array of microneedles and a mechanical actuator; (b) the mechanical actuator, upon release from constraint by the capsule, expands outwardly in a direction away from a central longitudinal axis of the mechanical actuator and drives the array of microneedles into penetrating engagement with a lining of the GI tract of the subject; (c) and wherein the penetrating engagement facilitates delivery of a payload via the microneedles.

Example 34 is the method of example(s) 32 or 33, wherein providing the expanding material comprises providing an expanding material and a piston, the expanding material and the medicament on opposing sides of the piston.

Example 35 is the method of any one of example(s) 32-34, wherein the expanding material is a bio-compatible super absorbent material.

Example 36 is the method of example(s) 32-35, wherein enclosing the medicament and the expanding material with the capsule comprises introduction into a pre-made capsule or application of coatings to form the capsule.

Example 37 is the method of example(s) 32-36, wherein the capsule comprises a mucoadhesive layer or an enteric coating.

Example 38 is the method of example(s) 32-36, wherein the capsule comprises a mucoadhesive layer and an enteric coating.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

For example, more or fewer steps of the processes described herein may be performed according to the present disclosure. Moreover, other structures may perform one or more steps of the processes described herein.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases in one example, in an example, in one implementation, or in an implementation, or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive conditions. In other words, A, B, C includes any or all of the following alternative combinations as appropriate for a particular usage: A alone; B alone; C alone; A and B only; A and C only; B and C only; and all three of A and B and C.

The invention claimed is:

1. A system for targeted delivery of a medicament to a gastrointestinal (GI) tract of a subject, comprising:
   (a) a medicament comprising biotherapeutics and/or nucleic acids;
   (b) a mucoadhesive layer surrounding the medicament, wherein the mucoadhesive layer is coated onto the medicament, wherein the mucoadhesive layer comprises one of pectin, sodium caboxymethyl cellulose, or carbopol; and
   (c) an enteric coating encasing the medicament and mucoadhesive layer, wherein the enteric coating comprises:
   a first layer comprising a polymer degradable by a pH of the GI tract, wherein the first layer is adjacent the mucoadhesive layer, wherein the polymer is selected from the group consisting of polylactic acid, nylon, polyester, and polyvinyl alcohol; and
   a second layer comprising a wax material digestible by a lipase, wherein the wax material comprises one of coconut oil or bees wax, wherein the second layer is an outer layer;
   wherein the enteric coating dissolves in less than one minute in a human duodenum at a dissolution rate from 5 $(mg/cm^3)/min$ to 26 $(mg/cm^3)/min$.

2. The system for targeted delivery of a medicament of claim 1, wherein a weight ratio of the polymer degradable by pH and the wax material digestible by lipase is from 0.3:1 to 1:1.

3. The system for targeted delivery of a medicament of claim 1, wherein the enteric coating encasing the medicament and mucoadhesive layer does not degrade at a pH of 1.5 to 4.0 in a human stomach.

4. The system for targeted delivery of a medicament of claim 1, wherein the mucoadhesive layer adheres to a wall of the GI tract of the subject.

5. The system for targeted delivery of a medicament of claim 1, wherein the enteric coating is degraded in less than one minute in a human duodenum at a dissolution rate from 5 $(mg/cm^3)/min$ to 26 $(mg/cm^3)/min$ exposing the mucoadhesive layer and the medicament to a wall of the GI tract.

6. The system for targeted delivery of a medicament of claim 1, further comprising:
- (d) a medicament needle system for delivering the medicament to the GI tract; and
- (e) an expanding element expandable in response to absorbing fluid for driving the medicament and medicament needle system out of the mucoadhesive layer.

7. A method of administering a medicament directly to the gastrointestinal (GI) tract of a subject, administering to the subject the system of claim 1.

8. The method of claim 7, wherein the system is administered orally to the subject.

9. The method of claim 7, wherein the medicament is administered selectively to the GI tract of the subject.

10. The method of claim 9, wherein the medicament is administered selectively to the duodenum of the subject.

11. A system for targeted delivery of a medicament to a gastrointestinal (GI) tract of a subject, comprising:
- (a) a medicament comprising biotherapeutics and/or nucleic acids, wherein the mucoadhesive layer comprises one of pectin, sodium caboxymethyl cellulose, or carbopol;
- (b) a medicament needle system for delivering the medicament to the GI tract;
- (c) a capsule at least partially encasing the medicament needle system; wherein the capsule comprises:
- a mucoadhesive layer surrounding the medicament needle system; and
- an enteric coating encasing the mucoadhesive layer, wherein the enteric coating comprises:
- a first layer comprising a polymer degradable by a pH of the GI tract, wherein the first layer is adjacent the mucoadhesive layer, wherein the polymer is selected from the group consisting of polylactic acid, nylon, polyester, or polyvinyl alcohol; and
- a second layer comprising a wax material digestible by a lipase, wherein the wax material comprises one of coconut oil or bees wax, wherein the second layer is an outer layer;
- wherein the enteric coating degrades in less than one minute in a human duodenum at a dissolution rate from 5 $(mg/cm^3)/min$ to 26 $(mg/cm^3)/min$; and
- (d) an expanding element expandable in response to absorbing fluid for driving the medicament and medicament needle system out of the capsule.

12. The system of claim 11, wherein the capsule at least partially surrounds the medicament and the capsule defines a first opening and a second opening, the first opening adjacent the medicament needle system and the second opening adjacent the expanding element.

13. The system of claim 12, wherein the enteric coating closes the first opening and the second opening.

14. The system of claim 11, wherein the expanding element comprises a super absorbent material configured to expand up to or greater than 400 times in size.

15. The system of claim 14, wherein the super absorbent material comprises polyacrylate.

16. The system of claim 14, wherein the super absorbent material is bio-compatible and expands in volume as fluid is absorbed by the super absorbent material.

17. The system of claim 16, wherein the expanding element further comprises a piston and wherein the super absorbent material and the medicament needle system are on opposing sides of the piston.

* * * * *